(12) United States Patent
Greene

(10) Patent No.: US 8,805,641 B2
(45) Date of Patent: Aug. 12, 2014

(54) WIRELESS SENSOR BASED QUANTITATIVE FALLS RISK ASSESSMENT

(75) Inventor: Barry R. Greene, Dublin (IE)

(73) Assignee: Intel-GE Care Innovations LLC, Roseville, CA (US)

(*) Notice: Subject to any disclaimer, the term of this patent is extended or adjusted under 35 U.S.C. 154(b) by 428 days.

(21) Appl. No.: 12/782,110

(22) Filed: May 18, 2010

(65) Prior Publication Data

US 2011/0288811 A1 Nov. 24, 2011

(51) Int. Cl.
*G01P 3/00* (2006.01)
*G01P 15/00* (2006.01)
*A61B 5/11* (2006.01)
*G06F 19/00* (2011.01)

(52) U.S. Cl.
CPC . *G01P 3/00* (2013.01); *G01P 15/00* (2013.01); *A61B 5/112* (2013.01); *A61B 5/1117* (2013.01); *A61B 5/1123* (2013.01); *G06F 19/3431* (2013.01)
USPC ........... 702/145; 702/141; 702/142; 702/160; 702/176

(58) Field of Classification Search
CPC ............. G01P 3/00; G01P 3/64; G01P 15/00; A61B 5/112; A61B 5/1117; A61B 5/1123; G06F 19/3431
USPC .......................... 702/141, 142, 160, 176, 188
See application file for complete search history.

(56) References Cited

U.S. PATENT DOCUMENTS

2005/0010139 A1* 1/2005 Aminian et al. ............. 600/595

OTHER PUBLICATIONS

Salarian, A., Horak, F., Zampieri, C., Carlson-Kuhta, P., Nutt, J., Aminian, K. iTUG, A Sensitive and Reliable Measure of Mobility. IEEE Transactions on Neural Systems and Rehabilitation Engineering [online], Apr. 2010 [retrieved on May 1, 2010]. Retrieved from the Internet: <http://ieeexplore.ieee.org/xpls/abs_all.jsp?arnumber=5446357&tag=1>.*
Sabatini, A., Martelloni, C., Scapellato, S., Cavallo, F. Assessment of Walking Features From Foot Inertial Sensing. IEEE Transactions on Biomedical Engineering [online], Mar. 2005 [retrieved on May 1, 2012]. Retrieved from the Internet: <http://ieeexplore.ieee.org/xpls/abs_all.jsp?arnumber=1396389>.*
Greene et al., "Falls Risk Assessment through quantitative analysis of TUG", First AMA-IEEE Medical Technology Conference on Individualized Healthcare, Mar. 21-23, 2010.
O'Donovan et al., "Shimmer: A new tool for temporal Gait analysis", 31st Annual International Conference of the IEEE EMBS, Sep. 2-6, 2009, pp. 3826-3829.
Zampieri et al., The instrumented timed up and go test: potential outcome measure for disease modifying therapies in Parkinson's disease, Journal Neurology Neurosurgery and Psychiatry, Feb. 1, 2010, pp. 171-176, vol. 81, No. 2.

(Continued)

*Primary Examiner* — Sujoy Kundu
*Assistant Examiner* — Paul D Lee
(74) *Attorney, Agent, or Firm* — Pillsbury Winthrop Shaw Pittman LLP

(57) ABSTRACT

Methods and systems may provide for a plurality of kinematic sensors to be coupled to a corresponding plurality of shanks of an individual, a processor, and a memory to store a set of instructions. If executed by the processor, the instructions can cause the system to calculate a timed up and go (TUG) time segment based on angular velocity data from the plurality of kinematic sensors. The instructions may also cause the system to calculate a derived parameter based on the angular velocity data, and generate a falls risk assessment based on at least one of the TUG time segment and the derived parameter.

24 Claims, 3 Drawing Sheets

(56) References Cited

OTHER PUBLICATIONS

Greene et al., "Quantitative Falls Risk Assessment Using the Timed Up and Go Test", IEEE Transactions on Biomedical Engineering, Dec. 2010, pp. 2918-2926, vol. 57, No. 12.

Greene et al., "Adaptive, estimation of temporal gait parameters using body-worn gyroscopes", 32nd Annual International Conference of the IEEE EMBS, Aug. 31-Sep. 4, 2010, pp. 1296-1299.

International Search Report and Written Opinion mailed Oct. 12, 2011, for PCT/US2011/036955.

Giansanti, Daniele, "Investigation of fall-risk using a wearable device with accelerometers and rate gyroscopes", Physiol. Meas, vol. 27, Sep. 11, 2006, pp. 1081-1090.

Giansanti, Daniele, et al., "Assessment of fall-risk by means of a neural network based on parameters assessed by a wearable device during posturography", Medical Engineering & Physics, vol. 30, 2008, pp. 367-372.

Higashi, Yuji et al., "Quantitative Evaluation of Movement Using the Timed Up-and-Go Test", IEEE Engineering in Medicine and Biology Magazine, Jul./Aug. 2008, pp. 38-46.

Narayanan, Michael R., et al., "Longitudinal Falls Risk Estimation using Triaxial Accelerometry", IEEE Trans., vol. X, No. Y, Jul. 2009, pp. 1-8.

Salarian, Arash., et al., "iTUG, a Sensitive and Reliable Measure of Mobility", IEEE Transactions on Neural Systems and Rehabilitation Engineering 2010, pp. 1-8.

Zampieri, Cris., et al., "The instrumented timed up and go test: potential outcome measure for disease modifying therapies in Parkinson's disease", J. Neurol. Neurosurg Psychiatry, vol. 81, 2010, pp. 171-176.

Weiss, Aner., et al., "Can an accelerometer enhance the utility of the Timed Up & Go Test when evaluating patients with Parkinson's disease?", Medical Engineering & Physics vol. 32, 2010, pp. 119-125.

\* cited by examiner

WIRELESS SENSOR BASED QUANTITATIVE FALLS RISK ASSESSMENT

BACKGROUND

1. Technical Field

Embodiments generally relate to falls risk assessments. More particularly, embodiments relate to the quantitative assessment of falls risk using body-worn kinematic sensors.

2. Discussion

Falls in the elderly may represent a substantial healthcare problem worldwide. Indeed, a significant percentage of people over seventy years of age experience a significant fall, and the frequency of falls increases with age and the level of frailty. The timed up and go (TUG) test was developed as a tool to screen for balance problems in older individuals. In the TUG test, the individual gets up from a chair, walks three meters, turns at a designated spot, returns to the seat and sits down, wherein the total time taken to perform the test may generally be considered as indicative of the frailty of the individual. While it may be generally inferred that elders with longer TUG times can be more likely to fall than those with shorter TUG times, there still remains considerable room for improvement with regard to the use of the TUG test to conduct falls risk assessments. In particular, there currently may be a limited understanding of which specific portions or segments of the TUG test provide its predictive power for falls.

BRIEF DESCRIPTION OF THE DRAWINGS

The various advantages of the embodiments of the present invention will become apparent to one skilled in the art by reading the following specification and appended claims, and by referencing the following drawings, in which:

DETAILED DESCRIPTION

Embodiments may provide for a system including a plurality of kinematic sensors to be coupled to a corresponding plurality of shanks of an individual, a processor, and memory to store a set of instructions. If executed by the processor, the instructions cause the system to calculate a timed up and go (TUG) time segment based on angular velocity data from the plurality of kinematic sensors, and calculate a derived parameter based on the angular velocity data. The instructions, if executed, may also cause the system to generate a falls risk assessment based on at least one of the TUG time segment and the derived parameter.

Embodiments may also provide for a computer readable storage medium including a set of instructions which, if executed by a processor, cause a computer to calculate a TUG time segment based on angular velocity data from the plurality of kinematic sensors, and calculate a derived parameter based on the angular velocity data. The instructions, if executed, may also cause a computer to generate a falls risk assessment based on at least one of the TUG time segment and the derived parameter.

Other embodiments can involve a method of conducting falls risk assessments in which a plurality of adaptive thresholds are calculated based on angular velocity data from a plurality of shank-mounted kinematic sensors. A plurality of heel-strike points and toe-off points may be detected based on the angular velocity data. The method may also provide for calculating a TUG time segment based on the plurality of heel-strike points and toe-off points, wherein the TUG time segment is at least one of a walk time, a turn time, and a return time. The walk time can identify an amount of time between a first step and a last step of a TUG test, the turn time can identify an amount of time between the first step and a turn step of the TUG test, and the return time can identify an amount of time between the turn step and the last step of the TUG test. In addition, the method may involve calculating a derived parameter based on the angular velocity data, wherein the derived parameter includes at least one of a temporal gait parameter and an angular velocity-based parameter. At least one of a spurious heel-strike point and a spurious toe-off point may also be rejected. The method may further provide for generating a falls risk assessment based on at least one of the TUG time segment and the derived parameter.

Figure 1:
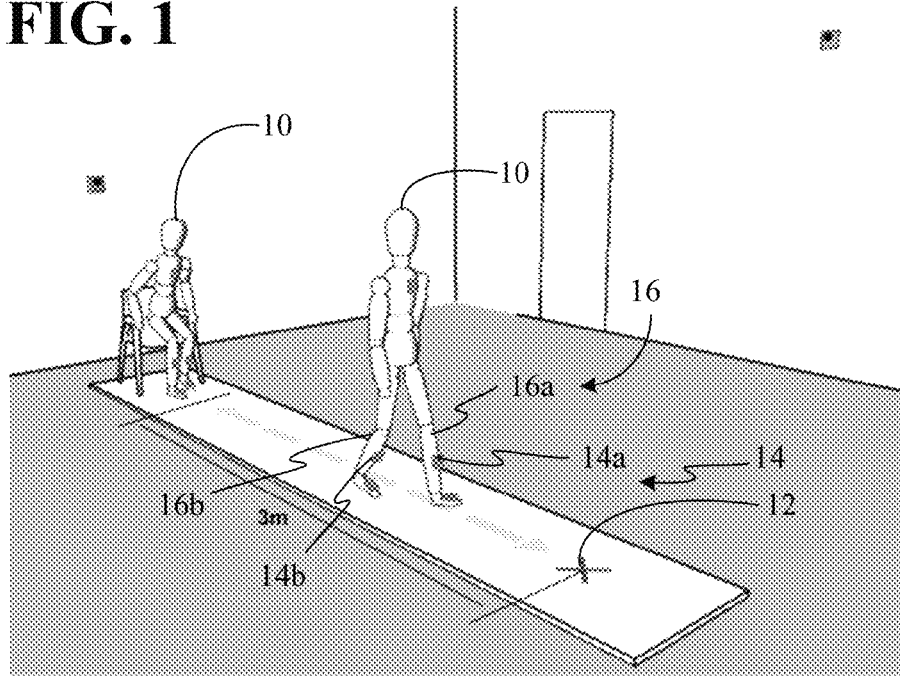
FIG. 1 is a perspective view of an example of an individual performing the timed up and go (TUG) test.

FIG. 1 shows an individual 10 performing a timed up and go (TUG) test in which the individual 10 gets up from a chair, walks three meters, turns at a designated spot 12, returns to the chair, and sits down. In the illustrated example, a pair of wireless kinematic sensors 14 (14a-14b) are coupled to the shanks (e.g., shins) 16 (16a-16b) of the legs of the individual 10, and output angular velocity data that can be used to automatically generate falls risk assessments. Thus, the illustrated approach could be used in primary or community care settings and may provide healthcare practitioners with a more detailed understanding of patients' falls risk. For example, some kinematic sensor-based parameters described herein may enable automated measurement of toe-clearance, vestibular impairment, muscular strength, etc., and might be used to identify deficits in one or more of these areas.

Each sensor 14, which might be mounted to the corresponding shank 16 below the patella via a tight fitting piece of clothing, a sock, an elastic tubular bandage, embedded in a shoe, etc., may include a tri-axial accelerometer and an add-on tri-axial gyroscope board. In particular, each sensor 14 may be positioned such that its measuring axis is aligned with the medio-lateral axis of the corresponding shank 16, and so that it is about half-way along the imaginary line between the Tibial Tuberosity (TT) and the Lateral Malleoulus (LM). In order to ensure that the angular velocity signal derived from the gyroscope has the correct polarity, the "skewness" of the signal (e.g., a measure of the asymmetry of the signal) may be calculated for each walk. If the skewness is less than zero, the gyroscope signal can be inverted to ensure the correct polarity of the signal. The sensors 14 may be programmed to sample each axis at a particular rate (e.g., 102.4 Hz) using firmware or other programmable technique, and to wirelessly transmit the angular velocity data using a protocol such as a low-rate wireless PAN (personal area network) or Bluetooth protocol.

Figure 2:
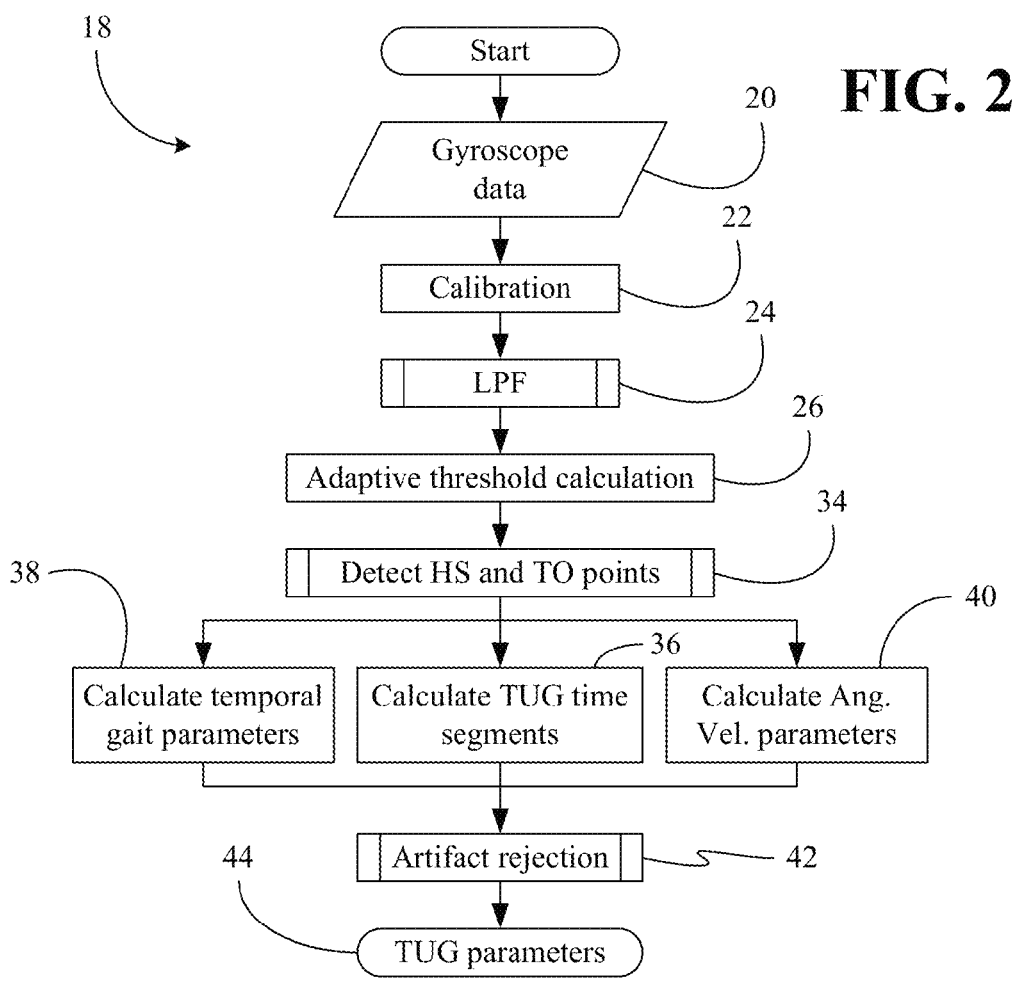
FIG. 2 is a flowchart of an example of a method of generating TUG parameters from gyroscope data according to an embodiment.

Turning now to FIG. 2, a method 18 of generating TUG parameters from gyroscope data is shown. The method 18 may be implemented in executable software as a set of logic instructions stored in a machine- or computer-readable medium of a memory such as random access memory (RAM), read only memory (ROM), programmable ROM (PROM), firmware, flash memory, etc., in fixed-functionality hardware using circuit technology such as application specific integrated circuit (ASIC), complementary metal oxide semiconductor (CMOS) or transistor-transistor logic (TTL) technology, or any combination thereof. For example, computer program code to carry out operations shown in method 18 may be written in any combination of one or more programming languages, including an object oriented programming language such as Java, Smalltalk, C++ or the like and conventional procedural programming languages, such as the "C" programming language or similar programming languages.

In the illustrated example, gyroscope data can be obtained using any appropriate mode of kinematic data acquisition. Upon receipt of the gyroscope data 20, processing block 22 may provide for using a sensor-to-segment offset orientation matrix (e.g., a rotation matrix) to calibrate the data 20 to derive acceleration and angular velocity vectors with respect to the coordinate axis of each kinematic sensor. Illustrated block 24 applies a low pass filter (LPF) to the calibrated data. In one example, the LPF might include a zero-phase $5^{th}$ order Butterworth filter (e.g., 20 Hz corner frequency).

Figure 3:
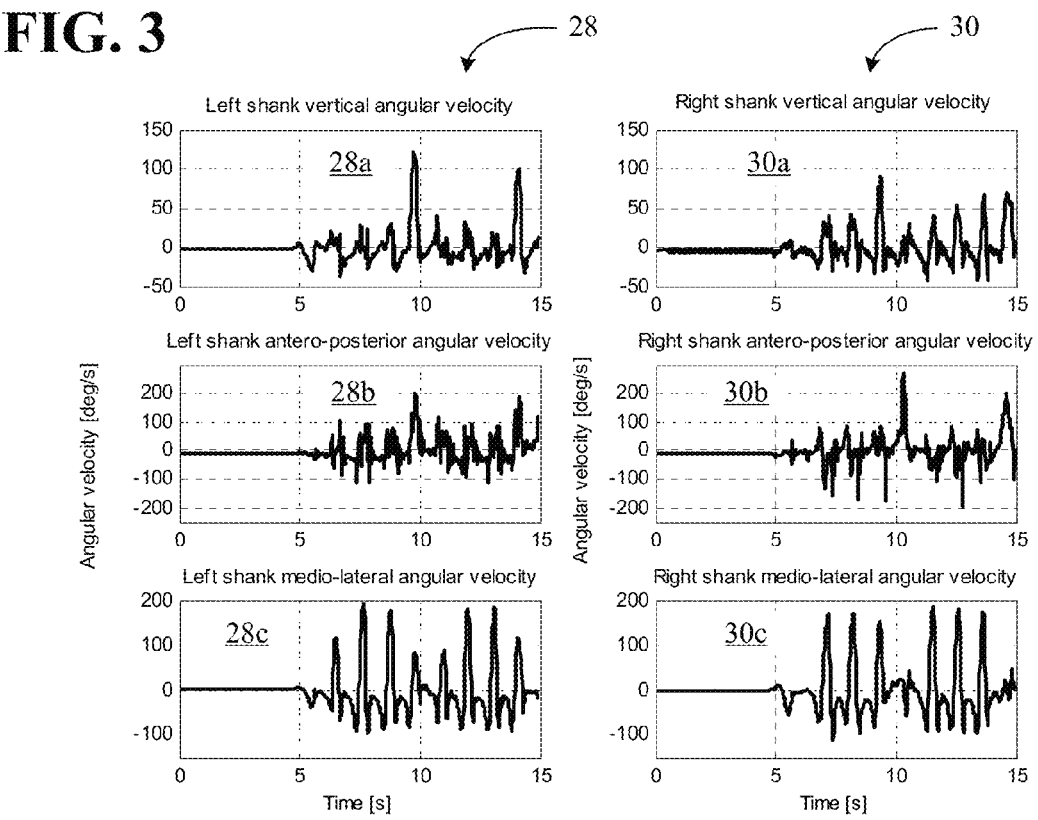
FIG. 3 are plots of examples of vertical, antero-posterior, and medio-lateral angular velocity according to an embodiment.

With reference to FIG. 3, a set of left shank signal plots 28 (28a-28c) and a set of right shank signal plots 30 (30a-30c) are shown. The plots 28 and 30 may represent tri-axial angular velocities corresponding to the motion of the individual 10 (FIG. 1) during the TUG test. In particular, plots 28a and 30a can be associated with vertical (V) angular velocity, plots 28b and 30b can be associated with antero-posterior (AP) angular velocity, and plots 28c and 30c can be associated with medio-lateral (ML) angular velocity. Generally, the data corresponding to the plots 28 and 30 may be used to detect events such as heel-strike points and toe-off points, which may in turn be used to calculate TUG time segments and various related temporal gait parameters, as will be discussed in greater detail. The data corresponding to the plots 28 and 30 can also be used to calculate and/or derive other angular velocity-based parameters useful in the falls risk assessment analysis.

Figure 4:
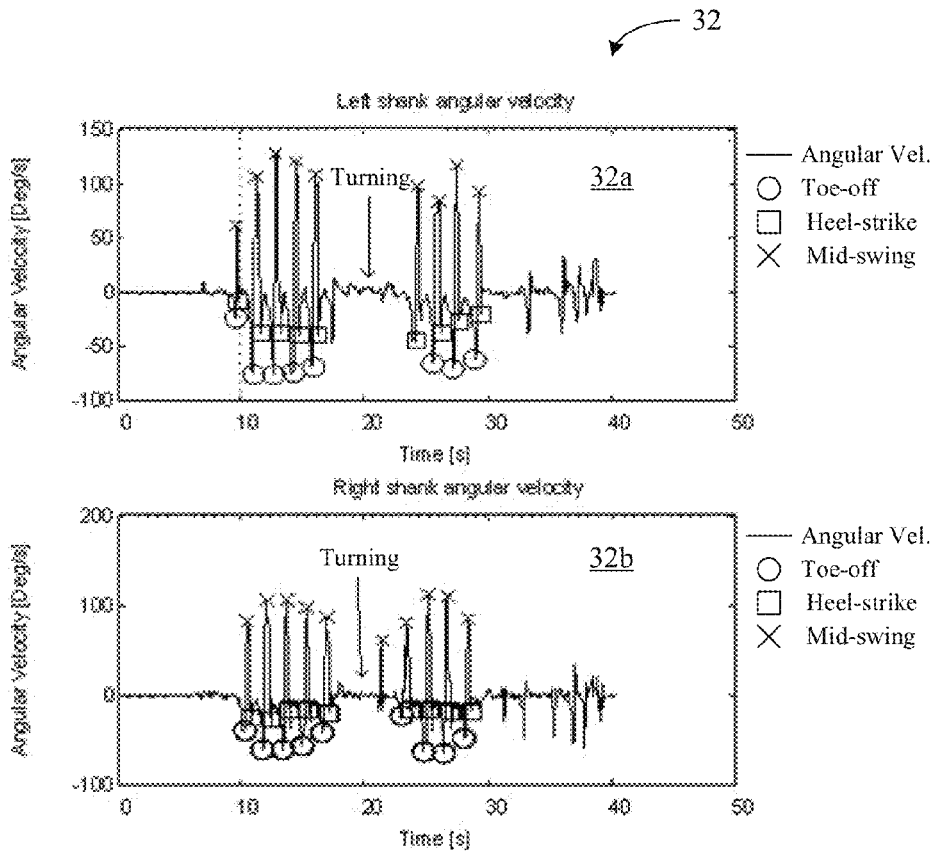
FIG. 4 are plots of examples of left and right shank medio-lateral angular velocity according to an embodiment.
Figure 5:
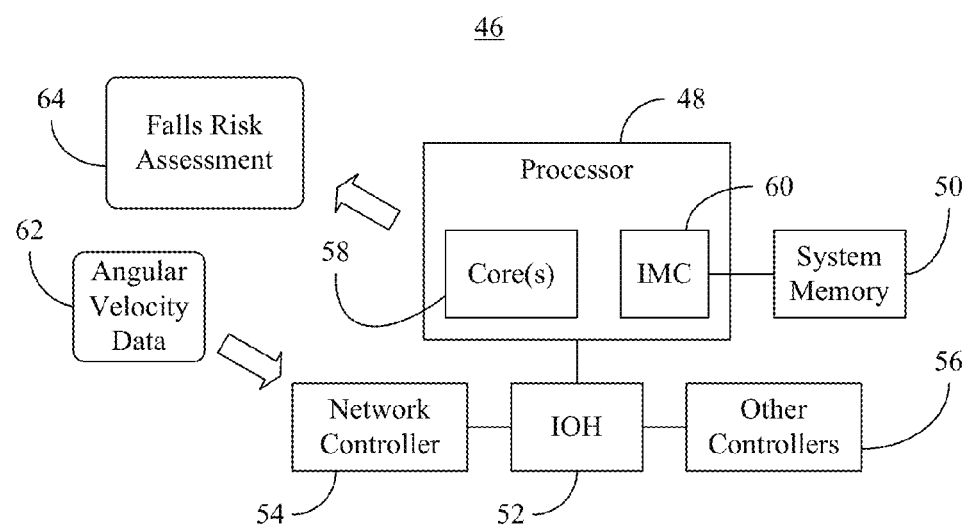
FIG. 5 is a block diagram of an example of a computing system according to an embodiment.

For example, FIG. 4 shows a pair medio-lateral angular velocity plots 32 (32a-32b) in which a series of heel-strike points and toe-off points can be detected from the signals. Generally, each toe-off point is reflected in a minimum value in the corresponding signal and is followed by a mid-swing point that can be identified via a maximum value in the signal. Each mid-swing point may then be followed by a heel-strike point that is reflected in another minimum value. In addition, turning points may be detected from a period of minimum amplitude in the signal between periods of cyclical activity.

Returning to FIG. 2, block 26 demonstrates that a plurality of adaptive thresholds may be created based on the angular velocity data, wherein the adaptive thresholds can be used to define the likely range of the heel-strike and toe-off points in the medio-lateral angular velocity data. Thus, restricting the angular velocity data based on the adaptive thresholds can ensure robust detection of these points over a variety of walking speeds. In particular, the following adaptive thresholds might be used:

Mid-swing point for each gait cycle: valid local maximum peaks may be required to have a preceding minimum of at least $th_1$ rad/sec less than the maximum medio lateral angular velocity ($\omega_{ML}$), wherein $th_1$ can be calculated as, $$th_1 = 0.6 \cdot \max(\omega_{ML}) \quad (1)$$

In addition, valid local maximum peaks can be required to be greater than $th_2$ rad/sec, wherein $th_2$ may be calculated as, $$th_2 = 0.8 \cdot \frac{1}{N}\sum_{i=1}^{N}(\omega_{ML_i} > \varpi_{ML}) \quad (2)$$

Moreover, if two maximum peaks are found within $t_1$ seconds of each other, only the greater maximum can be considered, wherein $t_1$ may be defined as 0.5 seconds or $f_s*1.5$ and $f_s$ is defined as the stride frequency.

Heel-strike points: valid local minimums may be required to have a preceding maximum of at least $th_3$ rad/sec greater than the local minimum, wherein $th_3$ can be calculated as, $$th_3 = 0.8 \cdot \left|\frac{1}{N}\sum_{i=1}^{N}(\omega_{ML_i} < \varpi_{ML})\right| \quad (3)$$

In addition, valid local minimums could be required to be less than $th_5$, wherein $th_5$ might be defined as, $$th_5 = \text{mean}(\omega_{ML}) \quad (4)$$

Toe-off points: valid local minimums can be required to be less than $th_4$, wherein $th_4$ may be calculated as, $$th_4 = 0.8 \cdot \frac{1}{N}\sum_{i=1}^{N}(\omega_{ML_i} < \varpi_{ML}) \quad (5)$$

In addition, valid local minimums could be required to have a preceding maximum of at least $th_6$ greater than the local minimum, wherein $th_6$ might be defined as, $$th_6 = 2th_3 \quad (6)$$

Heel-strikes and toe-offs: following mid-point detection, only data within $t_2$ seconds may be considered, wherein $t_2$ can be defined as 1.5 seconds or $f_s*1.5$. Specific values and ranges are provided herein to facilitate discussion only, and other values and ranges may be used as appropriate.

Block 34 may provide for detecting heel-strike and toe-off points based on the adaptive thresholds, as already discussed.

One or more TUG time segments can be calculated at block 36. The TUG time segments could include the walk time, the turn time and/or the return time. The walk time may identify the amount of time between the first step and the last step of the TUG test, wherein the first step can be defined by at least one of the first heel-strike point and the first toe-off point, and the last step can be defined by at least one of the last heel-strike point and the last toe-off point. The turn time can identify the amount of time between the first step and the turn step of the TUG test, wherein the turn step may be defined by at least one of a turn heel-strike point and a turn toe-off point. In one example, a per-shank turn time is calculated for each shank as the time of the median detected gait point (toe-off, heel-strike, mid-swing), and an overall turn time is calculated as the mean of the per-shank turn times. The return time may identify the amount of time between the turn step and the last step of the TUG test. Thus, the walk, turn and return times can be considered as time "segments" in that each calculation is a portion of the traditional TUG time, which is the entire amount of time required for the individual to complete the TUG test. As will be discussed below, the walk time, turn time and return time can be strong indicators of falls risk.

In addition to the TUG segments, one or more derived parameters may also be determined. For example, block 38 demonstrates that the derived parameters could include various other temporal gait parameters. Examples of such temporal gait parameters include, but are not limited to, the number of gait cycles, the number of steps taken, cadence, step time, and double support percentage. The number of gait cycles can be calculated as the number of right heel-strike points detected from the angular velocity signal during the TUG test minus one (i.e., the number of complete gait cycles). The cadence (e.g., steps per minute) can be calculated as sixty times the number of steps taken while performing the TUG test divided by the walk time (e.g., time taken to take the steps identified during the TUG test).

$$\text{Cadence} = 60 \cdot \left( \frac{\# \text{ Steps}}{\text{WalkTime}} \right) \quad (7)$$

Step time can be calculated as the time between the heel-strike point on one foot and the heel-strike point on the other foot. Double support may be determined by calculating the percentage of each gait cycle during which both feet are in contact with the ground (where the gait cycle time can be time between successive right heel strikes). As will be discussed below, the number of gait cycles, number of steps taken, cadence, double support percentage and step time can all be strong indicators of falls risk either alone or in combination with one or more other effects.

Other temporal gait parameters that may be derived include single support variability, step time variability, swing time variability, and walk-turn time ratio. Single support percentage for a foot may be defined as the swing duration of the other foot expressed as a percentage of gait cycle time, where the single support percentage data for each foot may be merged. The coefficient of variability (CV) for the single support percentage (as well as the other temporal gait parameters) can be calculated as a measure of single support variability. Thus, a "CV single support" parameter (expressed as a percentage) could be defined as the ratio of the standard deviation to the mean of the single support percentage. Similarly, a "CV step time" parameter may be calculated to reflect the step time variability as the ratio of the standard deviation to the mean of the step time. The swing time can be calculated as the time between a toe-off point and the heel-strike point on the same foot. Thus, the swing time variability ("CV swing time") could be expressed as the ratio of the standard deviation to the mean of the swing time. The walk-turn time ratio could be defined as the ratio of the time to turn to the time from turn (e.g., unity indicates the same time taken to walk to and from the turn). As will be discussed in greater detail, the single support variability, step time variability and walk-turn time ratio may be indicators of falls risk, particularly if combined with one or more other effects.

Block 40 demonstrates that in addition to the temporal gait parameters, the derived parameters may include one or more parameters that are obtained directly from the angular velocity signal in the medio-lateral (ML), antero-posterior (AP) and vertical (V) directions in order to capture characteristics of the signal during the TUG test in three dimensions. For example, these angular velocity-based parameters could include parameters to detect and analyze the speed and timing of the turn during the TUG test.

Walk angular velocity: the mean, minimum and maximum angular velocities (averaged across both shanks), expressed in degrees per second, may each be determined in the ML, AP and V directions (i.e., 3×3=nine parameters in the tri-axial set of angular velocities).

Linear velocity: the tri-axial set of angular velocities may also be multiplied by the height of the individual performing the TUG test in order to obtain a variable approximately proportional to the linear velocity of the shank. This approximation can be based on the formula for linear velocity, which equals the radius times angular velocity, wherein the radius is the leg length and height is assumed to be approximately proportional to the leg length. Thus, the linear velocity may be specifically related to the shank/foot of the individual as opposed to merely the trunk of the individual.

Mid-swing point amplitude (mean and range): the mean amplitude of the mid-swing points can be calculated as the mean angular velocity at each of the mid-swing points, while the range of mid-swing points may be defined as the difference in amplitude (in deg/s) between the largest and smallest mid-swing points on the angular velocity signal obtained for each shank. Thus, the range of mid-swing point amplitudes may capture variability in leg movement.

As will be discussed in greater detail, the walk angular velocity, linear velocity and mid-swing point amplitude parameters can be strong indicators of falls risk either alone or in combination with one or more other effects.

In addition, other angular velocity-based parameters such as turn angular velocity may be calculated. The turn angular velocity can be defined as the mean amplitude (taken across both shanks) of the angular velocity signal at the turn point for each shank. As will be discussed in greater detail, turn angular velocity may be an indicator of falls risk, particularly if combined with one or more other effects. The coefficient of variation (CV) may also be calculated for each angular velocity parameter in order to provide a measure of variation during the TUG test.

As already discussed, the temporal gait parameters and TUG time segments may be calculated from the gait characteristic points such as heel-strike and toe-off points. An artifact rejection routine may be employed at block 42 to remove spurious temporal parameters that might have been calculated from erroneous gyroscope data. The artifact rejection routine can also be designed to account for missing and extra HS and TO points detected by the adaptive TUG algorithm. Artifact rejection may be based on two strands: examining temporal sequence information, and examining times between successive characteristic points (e.g., "gait cycle information").

Temporal sequence information: once all characteristic points are detected in processing block 34, each point may be assigned a numerical label of one to four—1-right heel-strike, 2-left toe-off, 3-left heel-strike, 4-right toe-off. A correct gait cycle (if starting on a right heel strike) would then follow the sequence 1, 2, 3, 4. By subtracting each label from the previous label, spurious samples (e.g., samples not producing a difference equal to either −3 or 1) may be deemed artifacts and rejected.

Gait cycle information: the time between adjacent gait characteristic points may be calculated for each set of characteristic points (e.g., right HS, left TO, left HS, right TO). This calculation can be referred to as "gait cycle time". If the difference between any successive characteristic point is greater than a particular time threshold (e.g., 2.5 seconds), the associated characteristic point could be identified as an artifact. Similarly, if the difference between any successive characteristic point is zero seconds, the associated point may be flagged as an artifact. Furthermore, any gait parameters with a negative or zero value may also be rejected. The result may be a set of TUG parameters 44 that are highly reliable and can be used to effectively generate falls risk assessments.

Experimental Results

The gait and balance of community dwelling elderly adults was assessed using shank-mounted kinematic sensors while each individual performed the TUG test. Individuals were also evaluated using the Berg balance scale (BBS), and the above-described TUG time segments and other derived parameters were calculated based on the angular velocity data from the kinematic sensors. Table I below shows the mean and standard deviations of each parameter that provided significant ($p<0.05$) discrimination between patients with a history of falls and those without for fallers and non-fallers either alone (A), in combination with another effect (C), or both (B). Correlation between each parameter and the BBS score ($\rho$ BBS) and the manual TUG time ($\rho$ manual TUG) are also shown.

the association between females who are over seventy-five years of age and frailty has been shown to be stronger than those in males. The number of males with no history of falling in the data set was deemed insufficient to generate robust logistic regression models of males in two age categories. As a result, three separate logistic regression models were generated: 1) Males; 2) Females under seventy-five years of age; and 3) Females over seventy-five years of age.

Due to the large quantity of gyroscope derived variables, variables were blocked (e.g., grouped) in terms of general characteristics before performing the analysis. A series of logistic regression analyses with fall status as the dependent variable was carried out. Working with each block we performed a logistic regression analysis on each individual inde-

TABLE I

| Variable | Mean std (faller) | Mean std (non-faller) | $\rho$ BBS | $\rho$ manual TUG | Significance Alone (A) Combo (C) Both (B) |
|---|---|---|---|---|---|
| Walk Time (s) | 8.2 ± 3.4 | 6.1 ± 2.0 | −0.69 | 0.90 | B |
| Return time (s) | 4.4 ± 2.0 | 3.2 ± 1.2 | −0.69 | 0.89 | B |
| No Steps | 12.8 ± 3.8 | 10.6 ± 2.4 | −0.54 | 0.66 | A |
| Turn-Start Time (s) | 3.8 ± 1.5 | 2.9 ± 0.9 | −0.62 | 0.83 | A |
| Min ML angular velocity × Height | −181.7 ± 36.4 | −213.3 ± 56.9 | −0.45 | 0.55 | A |
| TUG recording time (s) | 15.6 ± 6.5 | 12.4 ± 5.1 | −0.53 | 0.67 | A |
| Min AP angular velocity × Height | −347.0 ± 93.6 | −400.9 ± 89.9 | −0.40 | 0.52 | A |
| No. gait cycles | 5.2 ± 1.9 | 4.2 ± 1.2 | −0.49 | 0.59 | B |
| Max V angular velocity × Height | 195.7 ± 57.5 | 228.5 ± 67.3 | 0.37 | −0.49 | A |
| Mean AP angular velocity × Height | 39.4 ± 13.7 | 47.8 ± 16.7 | 0.41 | −0.52 | A |
| Max ML angular velocity × Height | 292.0 ± 50.4 | 329.2 ± 71.9 | 0.45 | −0.52 | A |
| Mean V angular velocity × Height | 24.8 ± 10.0 | 30.5 ± 11.0 | 0.36 | −0.48 | A |
| Min V angular velocity × Height | −140.4 ± 53.4 | −177.6 ± 80.8 | −0.29 | 0.41 | A |
| Min ML angular velocity (deg/s) | −111.3 ± 21.9 | −126.8 ± 32.8 | −0.42 | 0.50 | A |
| Mean Vert. angular velocity (deg/s) | 15.2 ± 5.9 | 18.1 ± 6.4 | 0.35 | −0.46 | B |
| Max Vert. angular velocity (deg/s) | 119.6 ± 34.1 | 135.8 ± 39.4 | 0.35 | −0.46 | B |
| Mean AP angular velocity (deg/s) | 24.1 ± 8.1 | 28.4 ± 9.6 | 0.41 | −0.50 | A |
| Min AP angular velocity (deg/s) | −212.3 ± 55.6 | −238.3 ± 52.3 | −0.37 | 0.48 | A |
| Cadence (steps/min) | 99.2 ± 19.3 | 108.0 ± 19.3 | 0.44 | −0.63 | B |
| Mean ML angular velocity × Height | 46.5 ± 15.0 | 54.3 ± 17.6 | 0.39 | −0.45 | B |
| Min Vert. angular velocity (deg/s) | −85.6 ± 30.7 | −105.5 ± 48.0 | −0.28 | 0.38 | A |
| AP angular velocity max × Height | 347.3 ± 115.2 | 396.8 ± 132.4 | 0.36 | −0.45 | A |
| Max ML angular velocity (deg/s) | 178.8 ± 29.5 | 195.9 ± 43.1 | 0.41 | −0.46 | A |
| Mean ML angular velocity (deg/s) | 28.5 ± 9.0 | 32.3 ± 10.4 | 0.37 | −0.41 | B |
| Mean mid-swing points (deg/s) | 133.5 ± 24.6 | 143.9 ± 26.0 | 0.47 | −0.52 | B |
| Max AP angular velocity (deg/s) | 212.4 ± 68.6 | 235.6 ± 76.4 | 0.34 | −0.42 | A |
| Range of mid-swing points (deg/s) | 111.7 ± 30.5 | 125.1 ± 41.7 | 0.22 | −0.28 | B |
| Mean Double support (%) | 0.4 ± 0.2 | 0.5 ± 0.2 | 0.10 | −0.14 | A |
| Mean step time (s) | 0.7 ± 0.1 | 0.6 ± 0.1 | −0.16 | 0.26 | A |
| CV single support (%) | 22.9 ± 15.7 | 21.1 ± 19.2 | −0.10 | 0.12 | C |
| Walk-time ratio | 1.2 ± 0.3 | 1.1 ± 0.2 | −0.21 | 0.26 | C |
| CV swing time (s) | 28.1 ± 19.9 | 31.0 ± 22.0 | 0.09 | −0.06 | C |
| CV step time (s) | 42.0 ± 21.0 | 40.3 ± 22.9 | 0.13 | −0.16 | C |
| Turn angular velocity (deg/s) | 24.2 ± 50.9 | 26.3 ± 58.3 | 0.06 | −0.01 | C |

Generally, the TUG time segment parameters were strongly correlated with the manual TUG time including: return time ($\rho=0.89$, $p<0.001$), time of turn ($\rho=0.83$, $p<0.001$) and walk time ($\rho=0.90$, $p<0.001$). The parameters indicated in the table as having significance only in combination with another effect, were found to have a strong association with falls risk but did not show a strong correlation with the Berg score and manual TUG. Those parameters may therefore contain complementary information about the properties of standing, turning and walking associated with falls that are not captured by the BBS and manual TUG tests.

In particular, following initial non-parametric screening, logistic regression was used to test the predictive properties of each parameter, automatically derived during the TUG test. The entire sample was stratified by gender and age because pendent variable plus all two-way interactions, and retained only those which were significant ($p<0.05$) in each block.

The significant variables from each block were combined into a final model. Through logistic regression, all non-significant variables were eliminated. For comparison purposes, logistic regression models were also created in each of the three patient groups discussed above using only the values for each patient for manual TUG and BBS scores.

By stratifying model variables by age and gender, it emerged that although many of the reported variables showed significant discrimination between fallers and non-fallers, not every variable was significant in each of the three groups, suggesting there exist different properties of movement between fallers and non-fallers in each of the three groups. For example, gait variability based parameters such as swing time variability and single support variability may have a strong impact on falls risk in females seventy-five and over and interestingly both variables could have a strong interaction effect with patient's age in this grouping. Similarly, step time variability and single support variability might have a bearing on the falls risk for females under seventy-five.

By contrast, these gait variability features may not have a bearing on the falls risk in males. Variables related to gait velocity such as cadence, number of gait cycles and return time may be strongly associated with falls risk for this group. In particular, the time taken for the subject to walk back to the chair from the turn (return time) was found to have a very strong bearing on the falls risk for men in the population, whereas the time taken for the patient to walk to the turn (turn time) did not have as strong a relationship with falls risk. Accordingly, it may be inferred that male fallers have a tendency to walk more slowly after the turning phase of the TUG test than male non-fallers, which may suggest a link with muscular fatigue and frailty. Table II below summarized these findings.

TABLE II

| Model 1 (Male) | Model 2 (Female < 75) | Model 3 (Female ≥ 75) |
| --- | --- | --- |
| Mean ML angular velocity | CV single support | Log CV single support |
| Weight | CV step time | Log CV swing time |
| Return time | Walk time ratio | Age |
| Range mid-swing points | Height | Walk time |
| Cadence | Mean V angular velocity | Mean mid-swing points |
| Turn angular velocity | Max V angular velocity | Mean mid-swing points: Walk time |
| No. gait cycles | Age | Log CV swing time: Age |
| Mean AV ML × Height | CV single support: CV step time | Log CV single support: Age |
| Mean ML angular velocity: Weight | Walk time ratio: Height | |
| Range mid-swing points: Cadence | Mean V angular velocity: Max V angular velocity | |
| Turn angular velocity: Gait Cycles | | |
| Weight: Mean ML angular velocity × Height | | |

Thus, in the females under seventy-five model, age also showed significance (p<0.05) however as a main effect and not part of an interaction. In this model the older the female is, the greater the risk of falling. In addition to this main effect, there may be three two-way interaction effects; the first being that between single support variability and step time variability, which indicate that with the increase of this effect comes a decrease in falls risk. The second two-way interaction effect is between walk-time ratio and height, where an increase in their interaction effect can lead to an increase in falls risk. The third and last two-way interaction effect may be between mean vertical angular velocity and max vertical angular velocity, where an increase in their interaction effect may result in an increase in falls risk.

The females over seventy-five model interaction effects show that the prevalence of fallers can be much more evident in participants who take longer to complete the TUG test (e.g., walk time) and have a lower mean of mid-swing points. In addition to these findings, two other two-way interaction effects were found to be significant (p<0.05) within this model; these included an interaction effect of age with single support variability (log CV single support) and an interaction effect between age and swing time variability (log CV swing time—logs taken to more normally distribute the variable for the purposes of the logistic regression model). It is evident that the risk of being a faller in this category may be increased if the variation is low and the individual resides in the older range of the spectrum. As variation in log CV swing time increases above the mean, fallers have a reduced mean age, whereas non-fallers have an increased mean age. This data therefore shows that as swing time variability increases, fallers seem to be more prevalent amongst younger patients, where as in the non-faller group with an increase in variation we see a marked increase in prevalence as age increases. The risk of being a faller in this category may therefore be increased if variation is low and the individual resides in the older age-range of the spectrum.

The final model included all males in the data set. Due to limited sample size the male patients were not stratified by age. A larger cohort of community dwelling elderly males could yield, however, additional results on the effect of age on the reported gyroscope derived TUG parameters. The male model may be made up of one main effect and four two-way interaction effects. Return time can be the main effect and is highly correlated with manual TUG ($\rho=0.89$, $p<0.001$). Thus, the longer it takes a male subject to return to the chair after the turn, the higher the risk of falling. The first two-way interaction can involve mean ML angular velocity and weight, with an increase in their interaction leading to an increase in falls risk. The second two-way interaction may involve the range of mid-swing points and cadence. The higher the interaction effect between the range of mid-swing points and cadence, the lower the risk of falling. In the third interaction effect between gait cycles and turn angular velocity, an increase in the effect will may be indicative of an increase in falls risk. In the final two-way interaction effect between weight and mean ML angular velocity X height, an increase in the interaction effect may be indicative of a decrease in falls risk.

In addition to the above considerations, some of the calculated parameters may provide a mechanism to determine toe/foot clearance, wherein low toe/foot clearance can be strongly indicative of trip hazards and falls risk. For example, relatively low positive peaks in vertical angular velocity while walking and/or turning could indicate a falls risk.

In order to ensure an unbiased estimate of each model's falls prediction performance ten fold cross-validation was employed. In each stratified sample, male (N=77, fallers=32, non-fallers=45), female<75 (N=119, fallers=72, non-fallers=47) and female ≥75 (N=68, fallers=45 and non-fallers=23) a randomized 80% sample was taken to train the model with the significant variables identified in Table 1 and tested against the remaining 20%. The randomization was constrained to ensure the prevalence of fallers within the 20% test was of an adequate level. This was completed ten times with a different 80:20 mix each time for each of the three models. Accuracy (Acc), Sensitivity (Sens) and specificity (Spec) were the numerical metrics employed to quantify the performance of each validation. Sensitivity can be defined as the proportion of fallers (as labeled by the geriatrician evaluating the subject in the clinic) correctly identified by the model. Similarly, specificity can be defined as the proportion of non-fallers that are correctly identified by the model. Accuracy can then be defined as the overall percentage of patients correctly classified. Receiver operating characteristic (ROC) curves were generated for each logistic regression model using the test set probability outputs obtained by cross validation. The area under the ROC curve was also used as an index of each statistical model's performance. Table III below shows the data for the ROC curves.

TABLE III

|  | Gyroscope | | | | BBS | | | | TUG | | | |
| --- | --- | --- | --- | --- | --- | --- | --- | --- | --- | --- | --- | --- |
|  | Male | Female (Age < 75) | Female (Age >= 75) | Mean | Male | Female (Age < 75) | Female (Age >= 75) | Mean | Male | Female (Age < 75) | Female (Age >= 75) | Mean |
| Acc (%) | 80.0 | 72.5 | 77.9 | 76.8 | 63.1 | 57.5 | 63.6 | 61.4 | 60.6 | 57.5 | 63.6 | 60.6 |
| Sens (%) | 71.5 | 77.5 | 82.9 | 77.3 | 45.7 | 54.9 | 72.9 | 57.8 | 39.0 | 55.0 | 79.9 | 58.0 |
| Spec (%) | 89.0 | 66.0 | 72.8 | 75.9 | 76.5 | 62.0 | 54.2 | 64.2 | 87.8 | 59.2 | 47.3 | 64.8 |
| ROC area | 0.84 | 0.73 | 0.86 | 0.81 | 0.68 | 0.62 | 0.69 | 0.66 | 0.72 | 0.65 | 0.70 | 0.69 |

Thus, the male model had an ROC curve area of 0.84 while the female under and over seventy-five models had ROC curve areas of 0.73 and 0.86, respectively. In addition, the gyroscope derived model had an overall mean ROC curve area of 0.81, while the TUG and BBS based logistic regression models had ROC curve areas of 0.66 and 0.69, respectively.

Turning now to FIG. 6, a computing system 46 is shown having a processor 48, system memory 50, an input/output hub (IOH) 52, a network controller 54, and various other controllers 56. The system 46 could be part of a mobile platform such as a laptop, personal digital assistant (PDA), mobile Internet device (MID), wireless smart phone, media player, imaging device, etc., or any combination thereof. For example, the system 46 might be implemented in a wireless smart phone carried by an individual performing a TUG test in a primary care, community care or home setting. In addition, the system 46 may also be part of a fixed platform such as a personal computer (PC), server, workstation, etc. Thus, the processor 48 may include one or more processor cores 58 capable of executing a set of stored instructions, and an integrated memory controller (IMC) 60 configured to communicate with the system memory 50. The system memory 50 could include dynamic random access memory (DRAM) configured as a memory module such as a dual inline memory module (DIMM), a small outline DIMM (SODIMM), etc.

The illustrated IOH 52, sometimes referred to as a Southbridge of a chipset, functions as a host device and communicates with the network controller 54, which could provide off-platform communication functionality for a wide variety of purposes such as cellular telephone (e.g., W-CDMA (UMTS), CDMA2000 (IS-856/IS-2000), etc.), WiFi (e.g., IEEE 802.11, 1999 Edition, LAN/MAN Wireless LANS), Low-Rate Wireless PAN (e.g., IEEE 802.15.4-2006, LR-WPAN), Bluetooth (e.g., IEEE 802.15.1-2005, Wireless Personal Area Networks), WiMax (e.g., IEEE 802.16-2004, LAN/MAN Broadband Wireless LANS), Global Positioning System (GPS), spread spectrum (e.g., 900 MHz), and other radio frequency (RF) telephony purposes. In the illustrated example, the network controller 54 obtains angular velocity data 62 wirelessly (e.g., from a data aggregator over a Bluetooth connection), and provides the angular velocity data 62 to the processor 48 for further analysis. The illustrated processor 48 calculates TUG parameters 44 (FIG. 2) and generates falls risk assessments 64, which might also be gender, weight and/or age-based, as already discussed.

The other controllers 56 could communicate with the IOH 52 to provide support for user interface devices such as a display, keypad, mouse, etc. in order to allow a user to interact with and perceive information from the system 46.

Embodiments of the present invention are applicable for use with all types of semiconductor integrated circuit ("IC") chips. Examples of these IC chips include but are not limited to processors, controllers, chipset components, programmable logic arrays (PLA), memory chips, network chips, and the like. In addition, in some of the drawings, signal conductor lines are represented with lines. Some may be thicker, to indicate more constituent signal paths, have a number label, to indicate a number of constituent signal paths, and/or have arrows at one or more ends, to indicate primary information flow direction. This, however, should not be construed in a limiting manner. Rather, such added detail may be used in connection with one or more exemplary embodiments to facilitate easier understanding of a circuit. Any represented signal lines, whether or not having additional information, may actually comprise one or more signals that may travel in multiple directions and may be implemented with any suitable type of signal scheme, e.g., digital or analog lines implemented with differential pairs, optical fiber lines, and/or single-ended lines.

Example sizes/models/values/ranges may have been given, although embodiments of the present invention are not limited to the same. As manufacturing techniques (e.g., photolithography) mature over time, it is expected that devices of smaller size could be manufactured. In addition, well known power/ground connections to IC chips and other components may or may not be shown within the figures, for simplicity of illustration and discussion, and so as not to obscure certain aspects of the embodiments of the invention. Further, arrangements may be shown in block diagram form in order to avoid obscuring embodiments of the invention, and also in view of the fact that specifics with respect to implementation of such block diagram arrangements are highly dependent upon the platform within which the embodiment is to be implemented, i.e., such specifics should be well within purview of one skilled in the art. Where specific details (e.g., circuits) are set forth in order to describe example embodiments of the invention, it should be apparent to one skilled in the art that embodiments of the invention can be practiced without, or with variation of, these specific details. The description is thus to be regarded as illustrative instead of limiting.

The term "coupled" is used herein to refer to any type of relationship, direct or indirect, between the components in question, and may apply to electrical, mechanical, fluid, optical, electromagnetic, electromechanical or other connections. In addition, the terms "first", "second", etc. are used herein only to facilitate discussion, and carry no particular temporal or chronological significance unless otherwise indicated.

Those skilled in the art will appreciate from the foregoing description that the broad techniques of the embodiments of the present invention can be implemented in a variety of forms. Therefore, while the embodiments of this invention have been described in connection with particular examples thereof, the true scope of the embodiments of the invention should not be so limited since other modifications will become apparent to the skilled practitioner upon a study of the drawings, specification, and following claims.

I claim:

1. A method comprising:
obtaining, at a processor, a plurality of adaptive thresholds whose values change based on angular velocity data from a plurality of shank mounted kinematic sensors, wherein the plurality of adaptive thresholds defines a likely range of a plurality of heel-strike points and toe-off points in the angular velocity data;
detecting, at the processor, the plurality of heel-strike points and toe-off points based on the angular velocity data and based on the plurality of adaptive thresholds;
obtaining, at the processor, a first parameter based on a timed up and go (TUG) time segment, wherein the TUG time segment is determined based on the plurality of heel-strike points and toe-off points, and wherein the TUG time segment comprises at least one of a walk time, a turn time, a return time, a single support percentage, a step time, a walk-time ratio, or a swing time, wherein the walk time identifies an amount of time between a first step and a last step of a TUG test, wherein the turn time identifies an amount of time between the first step and a turn step of the TUG test, and wherein the return time identifies an amount of time between the turn step and the last step of the TUG test;
obtaining, at the processor, a second parameter based on a derived parameter, the derived parameter being determined based on the angular velocity data, wherein the derived parameter includes at least one of a temporal gait parameter or an angular velocity-based parameter; and
generating, at the processor, a falls risk assessment based on at least one of the first parameter or second parameter.

2. The method of claim 1, wherein the first step is defined by at least one of a first heel-strike point or a first toe-off point, the turn step is defined by at least one of a turn heel-strike point or a turn toe-off point, and the last step is defined by at least one of a last heel-strike point or a last toe-off point, wherein the first parameter is based on a statistical property of one or more values of the TUG time segment and wherein the second parameter is based on a statistical property of one or more values of the derived parameter, the statistical property including a minimum, maximum, mean, median, range, root mean square, or variability.

3. The method of claim 1, wherein the temporal gait parameter includes at least one of a cadence, a number of gait cycles, or a number of steps taken, and the angular velocity-based parameter includes at least one of a set of tri-axial angular velocities, a set of tri-axial linear velocities, or a mid-swing point angular velocity.

4. The method of claim 3, further including multiplying the set of tri-axial angular velocities by a height of an individual to obtain the set of tri-axial linear velocities.

5. The method of claim 1, further comprising:
obtaining, at the processor, an interaction parameter that measures an interaction between the first parameter and the second parameter, between the first parameter and another parameter, or between the second parameter and the another parameter;
generating, at the processor, the falls risk assessment based on the interaction parameter.

6. The method of claim 5, wherein the interaction parameter measures a two-way interaction between single support percentage variability and step time variability, between a walk-time ratio and height, between mean vertical angular velocity and max vertical angular velocity, between age of an individual and swing time variability, between return time and total TUG time, between mean angular velocity and weight of the individual, between range of mid-swing points and cadence, or between a number of gait cycles and turn angular velocity.

7. The method of claim 5, wherein the generating the falls risk assessment comprises increasing the falls risk assessment when a value of the interaction parameter increases.

8. The method of claim 5, wherein the generating the falls risk assessment comprises decreasing the falls risk assessment when a value of the interaction parameters increases.

9. A system comprising:
a plurality of kinematic sensors to be coupled to a corresponding plurality of shanks of an individual;
a processor; and
a memory to store a set of instructions which, if executed by the processor, cause the system to,
obtain a plurality of adaptive thresholds whose values change based on angular velocity data from the plurality of kinematic sensors, wherein the plurality of adaptive thresholds defines a likely range of a plurality of heel-strike points and toe-off points in the angular velocity data;
detect the plurality of heel-strike points and toe-off points based on the angular velocity data and based on the plurality of adaptive thresholds;
obtain a first parameter based on a timed up and go (TUG) time segment, wherein the TUG time segment is determined based on the plurality of heel-strike points and toe-off points;
obtain a second parameter based on a derived parameter, wherein the derived parameter is determined based on the angular velocity data; and
generate a falls risk assessment based on at least one of the first parameter or the second parameter.

10. The system of claim 9, wherein the TUG time segment comprises at least one of a walk time, a turn time, or a return time, wherein the walk time is to identify an amount of time between a first step and a last step of a TUG test, the turn time is to identify an amount of time between the first step and a turn step of the TUG test, and the return time is to identify an amount of time between the turn step and the last step of the TUG test.

11. The system of claim 10, wherein the first step is defined by at least one of a first heel-strike point and a first toe-off point, the turn step is defined by at least one of a turn heel-strike point and a turn toe-off point, and the last step is defined by at least one of a last heel-strike point and a last toe-off point, and the instructions, if executed, cause the system to detect the heel-strike points and toe-off points based on the angular velocity data.

12. The system of claim 11, wherein the instructions, if executed, further cause the system to reject at least one of a spurious heel-strike point and a spurious toe-off point.

13. The system of claim 9, wherein the derived parameter includes at least one of a temporal gait parameter and an angular velocity parameter.

14. The system of claim 13, wherein the temporal gait parameter includes at least one of a cadence, a number of gait cycles, and a number of steps taken.

15. The system of claim 13, wherein the angular velocity-based parameter includes at least one of a set of tri-axial angular velocities, a set of tri-axial linear velocities, and a mid-swing point angular velocity.

16. The system of claim 15, wherein the instructions, if executed, further cause the system to multiply the set of tri-axial angular velocities by a height of the individual to obtain the set of tri-axial linear velocities.

17. A non-transitory computer readable storage medium comprising a set of instructions which, if executed by a processor, cause a computer to:
   obtain a plurality of adaptive thresholds whose values change based on angular velocity data from a plurality of kinematic sensors, wherein the plurality of adaptive thresholds defines a likely range of a plurality of heel-strike points and toe-off points in the angular velocity data;
   detect the plurality of heel-strike points and toe-off points based on the angular velocity data and based on the plurality of adaptive thresholds;
   obtain a first parameter based on a timed up and go (TUG) time segment, wherein the TUG time segment is determined based the plurality of heel-strike points and toe-off points;
   obtain a second parameter based on a derived parameter, wherein the derived parameter is determined based on the angular velocity data; and
   generate a falls risk assessment based on at least one of the first parameter or the second parameter.

18. The non-transitory computer-readable medium of claim 17, wherein the TUG time segment comprises at least one of a walk time, a turn time, or a return time, wherein the walk time is to identify an amount of time between a first step and a last step of a TUG test, the turn time is to identify an amount of time between the first step and a turn step of the TUG test, and the return time is to identify an amount of time between the turn step and the last step of the TUG test.

19. The non-transitory computer-readable medium of claim 18, wherein the first step is defined by at least one of a first heel-strike point and a first toe-off point, the turn step is defined by at least one of a turn heel-strike point and a turn toe-off point, and the last step is defined by at least one of a last heel-strike point and a last toe-off point, and the instructions, if executed, cause a computer to detect the heel-strike points and toe-off points based on the angular velocity data.

20. The non-transitory computer-readable medium of claim 19, wherein the instructions, if executed, further cause a computer to reject at least one of a spurious heel-strike point and a spurious toe-off point.

21. The non-transitory computer-readable medium of claim 17, wherein the derived parameter includes at least one of a temporal gait parameter and an angular velocity-based parameter.

22. The non-transitory computer-readable medium of claim 21, wherein the temporal gait parameter includes at least one of a cadence, a number of gait cycles and a number of steps taken.

23. The non-transitory computer-readable medium of claim 21, wherein the angular velocity-based parameter is to include at least one of a set of tri-axial angular velocities, a set of tri-axial linear velocities, and a mid-swing point angular velocity.

24. The non-transitory computer-readable medium of claim 23, wherein the instructions, if executed, further cause a computer to multiply the set of tri-axial angular velocities by a height of an individual to obtain the set of tri-axial linear velocities.

* * * * *